(12) United States Patent
Fabien

(10) Patent No.: US 10,589,027 B2
(45) Date of Patent: *Mar. 17, 2020

(54) AUTOINJECTOR

(71) Applicant: APTAR FRANCE SAS, Le Neubourg (FR)

(72) Inventor: David Fabien, Plouarzel (FR)

(73) Assignee: APTAR FRANCE SAS, Le Neubourg (FR)

( * ) Notice: Subject to any disclaimer, the term of this patent is extended or adjusted under 35 U.S.C. 154(b) by 458 days.

This patent is subject to a terminal disclaimer.

(21) Appl. No.: 15/323,275

(22) PCT Filed: Jul. 2, 2015

(86) PCT No.: PCT/FR2015/051827
§ 371 (c)(1),
(2) Date: Dec. 30, 2016

(87) PCT Pub. No.: WO2016/001592
PCT Pub. Date: Jan. 7, 2016

(65) Prior Publication Data
US 2018/0185581 A1    Jul. 5, 2018

(30) Foreign Application Priority Data

Jul. 4, 2014  (FR) .................................... 14 56432

(51) Int. Cl.
*A61M 5/20* (2006.01)
*A61M 5/315* (2006.01)
*A61M 5/32* (2006.01)

(52) U.S. Cl.
CPC ........ *A61M 5/2033* (2013.01); *A61M 5/3157* (2013.01); *A61M 5/326* (2013.01);
(Continued)

(58) Field of Classification Search
CPC .. A61M 5/2033; A61M 5/3167; A61M 5/326; A61M 2005/206; A61M 2005/208; A61M 2005/2086
See application file for complete search history.

(56) References Cited

U.S. PATENT DOCUMENTS

2005/0277886 A1   12/2005  Hommann et al.
2008/0195056 A1*   8/2008  Bishop ................ A61M 5/2033
                                                            604/218

FOREIGN PATENT DOCUMENTS

EP        2 705 862 A1    3/2014
WO    2009/010591 A2    1/2009
(Continued)

OTHER PUBLICATIONS

International Preliminary Report on Patentability dated Jan. 19, 2017, issued by the International Bureau and corresponding application No. PCT/FR2015/051827.
(Continued)

*Primary Examiner* — Nathan R Price
*Assistant Examiner* — Tasnim Mehjabin Ahmed
(74) *Attorney, Agent, or Firm* — Sughrue Mion, PLLC

(57) ABSTRACT

An autoinjector having a body (1, 2), a reservoir (S) including a piston, a piston rod (5) movable between a rest position and an injection position, an actuator spring (6) urging the piston rod (5) towards the injection position, and a force-adjustment system (7, 8) to exert a force (F2) on the piston rod (5), adding to the force exerted by the spring (6) at the beginning of injection. The system has two pivot members (7) co-operating with the piston rod (5), the pivot members (7) connected together by two resilient elements (8). The body (1, 2) includes a sleeve (3), the pivot members (7) pivotally mounted on the sleeve (3) to pivot about stationary pins (79). The autoinjector includes an end-of-injection indicator that includes an indication portion movable and/or
(Continued)

deformable relative to the body (1, 2) to co-operate with a viewing window after the end of injection.

19 Claims, 7 Drawing Sheets

(52) U.S. Cl.
CPC . *A61M 2005/206* (2013.01); *A61M 2005/208* (2013.01); *A61M 2005/2086* (2013.01); *A61M 2005/3247* (2013.01); *A61M 2205/581* (2013.01); *A61M 2205/583* (2013.01)

(56) References Cited

FOREIGN PATENT DOCUMENTS

| WO | 2011/043714 | A1 | | 4/2011 | |
|----|-------------|-----|---|--------|------------|
| WO | 2011/101382 | A1 | | 8/2011 | |
| WO | WO-2012045838 | A1 | * | 4/2012 | .......... A61M 5/2033 |
| WO | 2015/001280 | A1 | | 1/2015 | |

OTHER PUBLICATIONS

International Search Report of PCT/FR2015/051827, dated Oct. 26, 2015. [PCT/ISA/210].

* cited by examiner

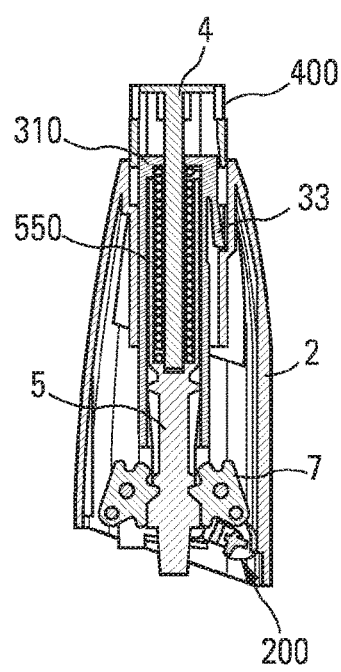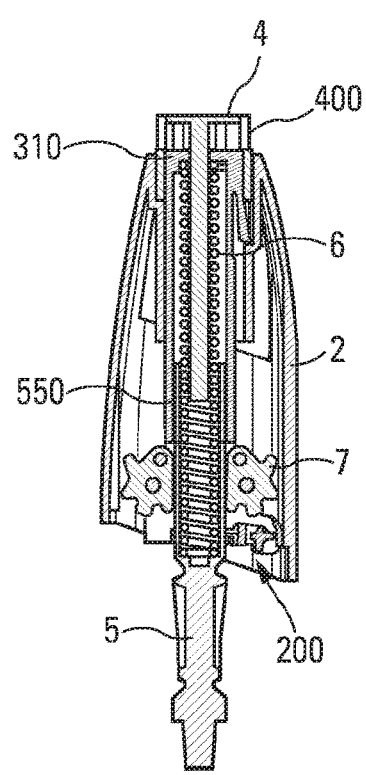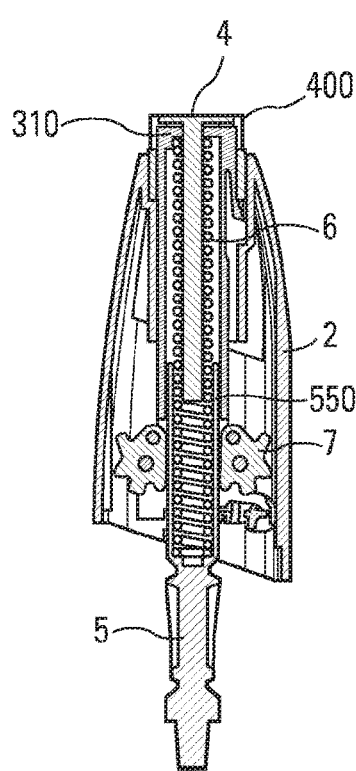
Fig. 15  Fig. 16  Fig. 17
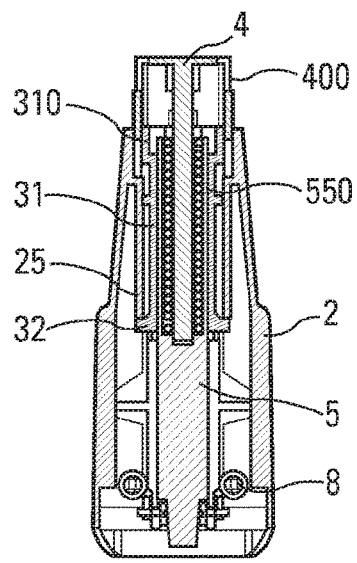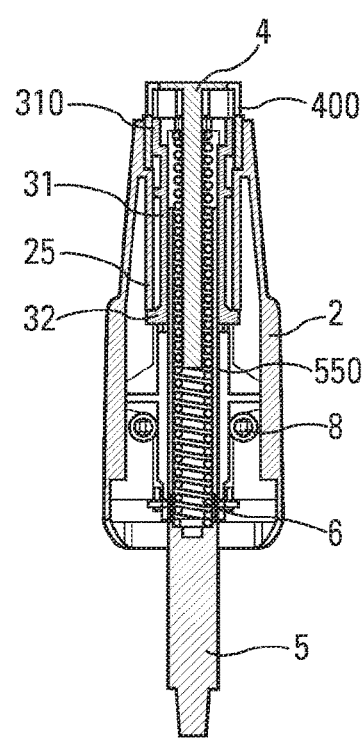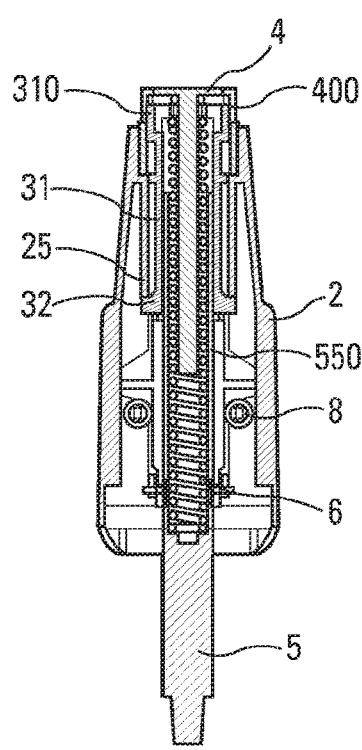
Fig. 18  Fig. 19  Fig. 20

AUTOINJECTOR

CROSS REFERENCE TO RELATED APPLICATIONS

This application is a National Stage of International Application No. PCT/FR2015/051827 filed Jul. 2, 2015, claiming priority based on French Patent Application No. 1456432, filed Jul. 4, 2014, the contents of all of which are incorporated herein by reference in their entirety.

BACKGROUND OF THE INVENTION

The present invention relates to an autoinjector.

Autoinjectors are well known in the prior art. The purpose of such devices is mainly to inject the contents of a syringe automatically into a patient's body. Various systems exist for making the penetration of the needle into the body of the patient and the injection of the fluid contained in the syringe automatic. Autoinjectors are relatively complex devices that must satisfy a certain number of constraint requirements in order to be reliable. The robustness of the device, its handling, and its ease of use for the user are also important elements. In addition, since most autoinjectors are for single use, the cost of manufacture and of assembly is also a factor that needs to be taken into account.

Numerous autoinjectors exist on the market, but they all present a certain number of drawbacks.

Thus, for autoinjectors that use the same spring both for initial pricking then for injection proper, the spring must be sufficiently strong to guarantee the injection stage in full. This is particularly true given that a relatively large force is generally required at the beginning of the injection stage, in order to start the movement of the piston of the syringe. As a result, the spring delivers its maximum power during pricking, which may make the pricking stage painful. Furthermore, with such a spring that is very powerful during pricking, there exists a significant risk of breaking the collar of the syringe, in particular when it is a glass syringe.

In addition, it may be desirable to have a visual and/or audible indication to inform the user that injection has terminated.

An object of the present invention is to provide an autoinjector that does not have the above-mentioned drawbacks, and that makes it possible to satisfy the various major requirements and constraints for safe and reliable use of the autoinjector.

Another object of the present invention is to provide an autoinjector that is reliable and safe in use, that makes it possible to guarantee that all of the fluid is dispensed to the desired location, that informs the user in reliable manner that injection has ended, and that is simple and inexpensive to manufacture and to assemble.

SUMMARY OF CERTAIN EMBODIMENTS OF THE INVENTION

The present invention thus provides an autoinjector comprising a body, and a reservoir containing fluid and including a piston and a needle, such as a pre-filled syringe, said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force F2 on said piston rod, said force F2 adding to the force exerted by said actuator spring on said piston rod at the beginning of injection, so as to amplify the force exerted on said piston by said piston rod at the beginning of injection, said force-adjustment system comprising two pivot members that co-operate with said piston rod, said pivot members being connected together by two resilient elements, said body including a sleeve, said pivot members being pivotally mounted on said sleeve to pivot about stationary pins, said autoinjector including a visual and/or audible indicator that is adapted to inform the user that injection has ended, said indicator being formed by and/or fastened to said sleeve and including an indication portion that is movable and/or deformable relative to said body so as to co-operate with at least one viewing window of said autoinjector after the end of injection.

Advantageously, said resilient elements are fastened to said pivot members via parallel movable pins, such as rods having two side edges, that are formed on said pivot members.

Advantageously, when the piston rod moves towards its injection position, said movable pins are arranged behind said stationary pins in the travel direction of said piston rod, said loaded resilient elements, at the beginning of travel of the piston rod towards its injection position, causing said pivot members to pivot in such a manner as to relax said resilient elements, thereby creating an amplification force F2 at the beginning of injection.

Advantageously, each pivot member includes a plurality of projections that are adapted to co-operate with a plurality of radial projections of the piston rod.

Advantageously, during pricking, the piston rod co-operates with the piston of the reservoir so as to move said reservoir relative to the body.

Advantageously, prior to injection, said piston rod is initially moved by said actuator spring between said rest position and a pricking position in which said piston rod has moved said reservoir relative to said body so as to perform pricking.

Advantageously, during pricking, the piston rod co-operates with the piston of the reservoir so as to move said reservoir relative to the body.

Advantageously, when the piston rod moves from its rest position towards its pricking position, said movable pins are arranged in front of said stationary pins in the travel direction of said piston rod, said piston rod, at the end of travel towards its pricking position, causing said pivot members to pivot so as to load said resilient elements, thereby creating a braking force F1 at the end of pricking, said force F1 being opposed, at the end of pricking, to the force exerted by said actuator spring on said piston rod, so as to decrease the force exerted on said reservoir by said piston rod at the end of pricking.

Advantageously, said autoinjector is actuated by an axial button.

Advantageously, said at least one viewing window is formed in said axial button.

Advantageously, said axial button includes a single viewing window that is arranged in a sloping axial end wall of said axial button.

In a variant, said axial button includes a plurality of viewing windows, distributed around the outer axial end edge of said axial button.

In another advantageous embodiment, said at least one viewing window is formed in said body.

Advantageously, said indicator is formed by said sleeve, including a single-piece axial projection that forms said indication portion of the indicator.

In a variant, said indicator is formed by a pivotable indicator element that is pivotally mounted on said sleeve, an end portion of said pivotable indicator element forming said indication portion of the indicator.

Advantageously, said pivotable indicator element is pivoted by said pivot members at the end of injection.

Advantageously, said sleeve includes at least one axial tab that is radially deformable and that co-operates with said body, said axial tab being prevented from deforming by said piston rod prior to and during movement of said piston rod, thus blocking any axial movement of said sleeve relative to said body, said piston rod releasing said blocking at the end of injection, such that said axial tab deforms radially inwards, enabling said sleeve to move axially relative to said body so as to provide a visual and/or audible indication.

BRIEF DESCRIPTION OF THE DRAWINGS

These characteristics and advantages and others of the present invention appear more clearly from the following detailed description, given by way of non-limiting examples, and with reference to the accompanying drawings, and in which:

FIGS. 15, 16 and 17 are diagrammatic section views showing a visual and or audible indicator in a first embodiment of the invention;

FIGS. 18, 19 and 20 are diagrammatic side views showing the indicator of FIGS. 15 to 17;

DESCRIPTION OF THE PREFERRED EMBODIMENTS

Figure 1:
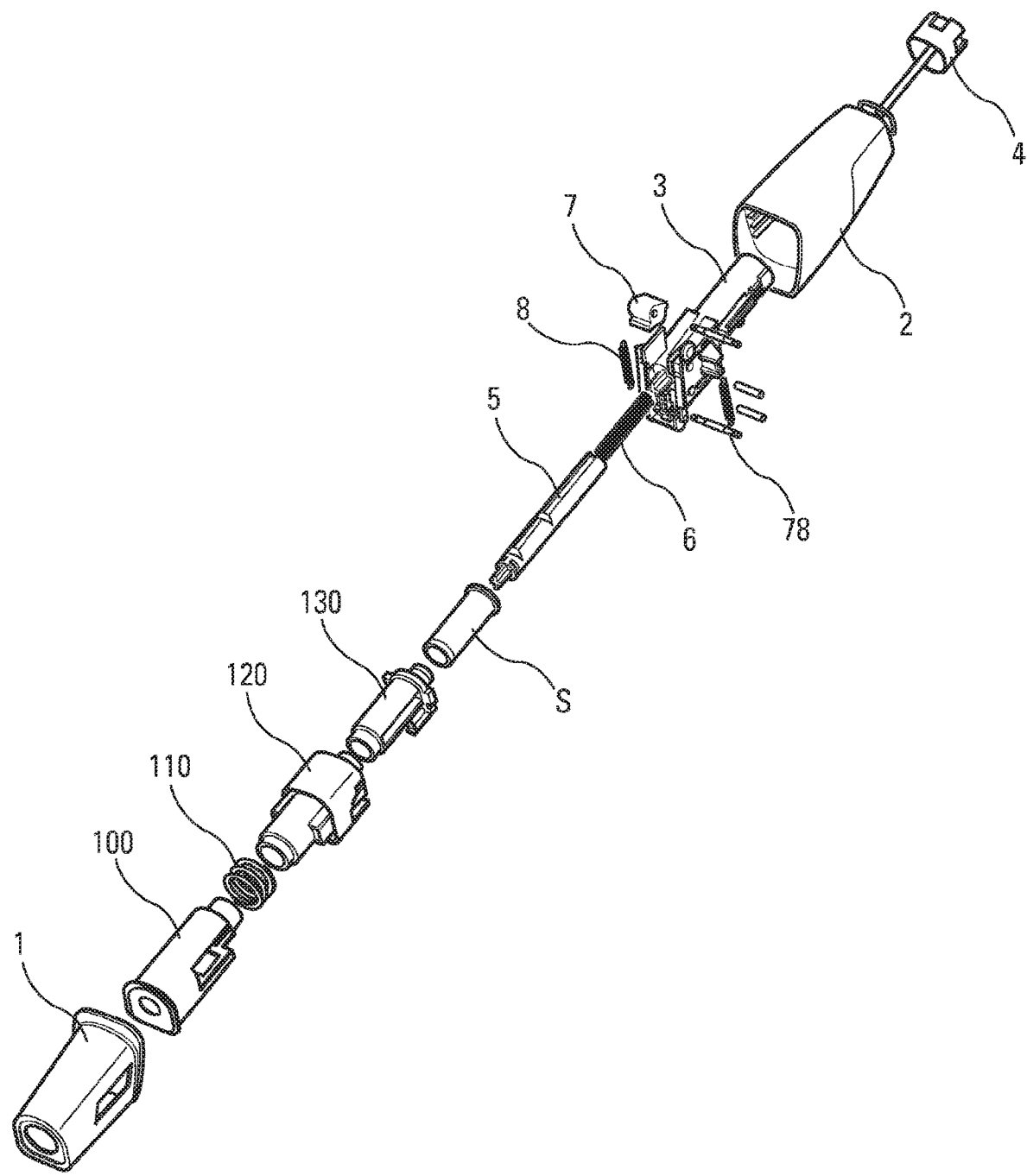
FIG. 1 is an exploded diagrammatic perspective view of the components of an autoinjector, in an advantageous embodiment.

The autoinjector is described below with reference to several advantageous embodiments. It should nevertheless be observed that autoinjectors, which are complex appliances, comprise a plurality of modules for performing a plurality of functions. The various modules may be used separately and independently of one another, without necessarily being combined with the other modules, and in particular they could be used in autoinjectors of shape that is different from the shape shown in the drawings. Furthermore, it should be observed that the drawings are diagrammatic views, which do not necessarily represent the exact shape of the components of an autoinjector, and they are not necessarily to scale, in particular for purposes of clarity. In addition, the drawings do not necessarily represent all of the component elements of an autoinjector, but only the elements necessary for operation of the present invention. Thus, various additional and/or complementary elements and modules could be associated with the autoinjector shown in the figures.

With reference to FIG. 1, the various components of the autoinjector, in an advantageous embodiment, are shown in an exploded view.

In the order of the numerical references, the autoinjector comprises a lower body 1, an upper body 2 containing a sleeve 3, an axial actuator button 4, a piston rod 5, an actuator spring 6, and two pivot members 7 that are interconnected by means of two resilient elements 8, which are preferably in the form of springs.

It should be observed that the lower and upper bodies could be replaced by a single body. Alternatively, a body constituted by more than two body portions may also be envisaged.

Figure 2:
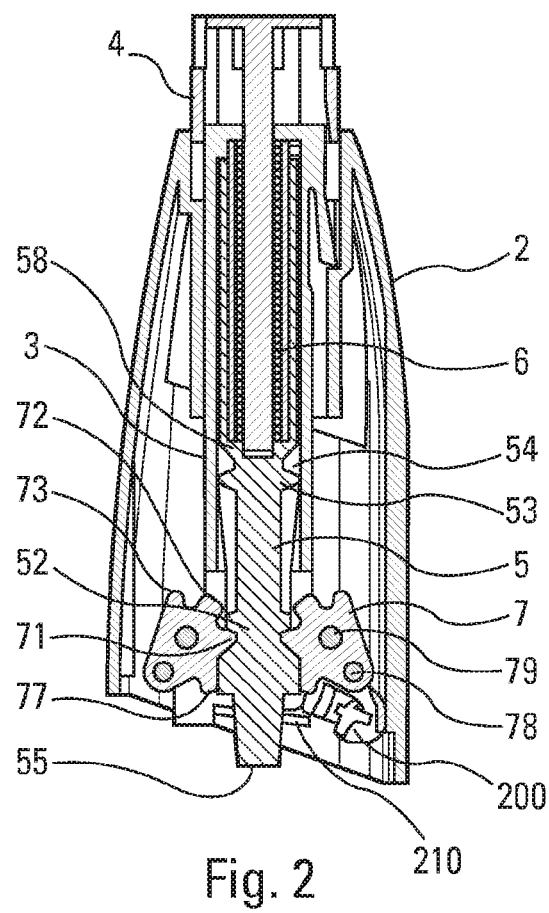
FIG. 2 is a section view of a detail of the FIG. 1 device.
Figure 3:
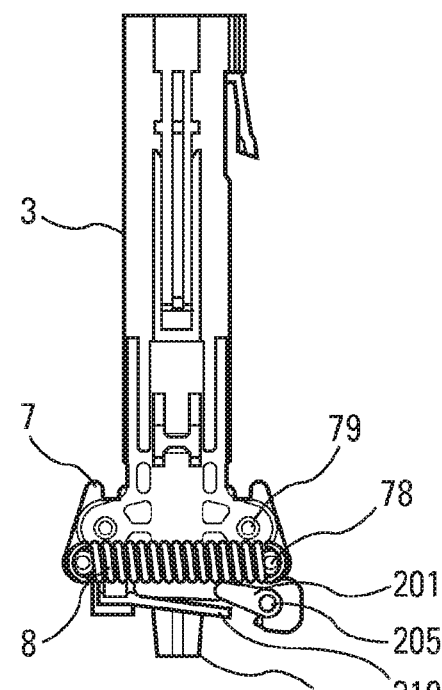
FIG. 3 is a side view of a detail of a portion of the FIG. 1 device.

The sleeve 3 may be clipped in the upper body 2 by means of a clip 33, which can be seen in particular in FIGS. 2 and 3.

A reservoir S is inserted into said autoinjector, in particular into its lower body 1. The reservoir S contains fluid and includes a piston and a needle (not shown in this embodiment). The piston is adapted to move in said reservoir S so as to inject the fluid through said needle.

The present description is made with reference to a syringe S that may be of any type. More generally, it is understood that the term "syringe" in the present description encompasses any type of reservoir associated with a needle. Preferably, the reservoir S is a pre-filled syringe.

The lower body 1, at its leading end (in the travel direction of the syringe S), includes an opening through which the needle passes during the pricking stage.

The lower body 1 contains an actuator sleeve 100 having an axial end surface 105 that is in contact with the part of the user's body where injection should take place. After actuation, the actuator sleeve 100 covers the needle of the syringe S so as to avoid any risk of pricking with said needle. The actuator sleeve 100 is adapted to slide relative to said lower body 1 between an initial rest position in which it projects axially out from said lower body 1 prior to actuation, an actuated position in which it moves axially towards the inside of said lower body 1, and a final safety position in which it once again projects out from said lower body 1, so as to cover the needle of the syringe S after injection. It should be observed that the final safety position may be identical to the initial rest position, or, in a variant, the two positions may be different, e.g. with the actuator sleeve 100 axially extending out from said lower body 1 in said final safety position further than in said initial rest position. The actuator sleeve 100 is advantageously urged axially towards the outside of said lower body 1 by a spring 110.

The lower body 1 may also contain an inner body 120 that is able to receive a reservoir support element 130 into which said syringe S is inserted.

The upper body 2 is fastened to the lower body 1 and it may receive a central sleeve 3 that is adapted to house the piston rod 5 and the spring 6.

The axial actuator button 4 may be mounted to slide axially relative to the upper body 2, and in contact with the piston rod 5. Thus, by pressing on the axial button 4 so as to drive it axially into the upper body 2, the piston rod 5 is moved axially, thereby making it possible to actuate the device as described below. In a variant, the axial button could be replaced by a lateral button.

The piston rod 5 includes a trailing portion 54 and a leading end 55 in the travel direction of the piston rod 5 in the upper body 2.

In this embodiment, the trailing portion 54 defines a tubular portion that receives the spring 6 and a portion of the axial button 4.

The purpose of the leading end 55 is to contact the piston of the syringe S, so as to move said piston and thus inject the fluid contained in the syringe S through the needle.

The piston rod 5 may also include a plurality of radial projections 52, 53: a first radial projection 52, that is close to the leading end 55, and that defines a shoulder-forming leading surface 51; and a second radial projection 53, that is axially offset from said first radial projection 52 towards the trailing end 54, and that defines both a leading surface and a trailing surface. Naturally, this is only an embodiment example, and a person skilled in the art is capable of making the radial projections and shoulders in a way that is different from the way shown in the drawings. In particular, said radial projections 52, 53 are not necessarily in the leading portion of the piston rod 5, as shown in the drawings, but they could be made on another portion of the piston rod 5. Indentations could alternatively replace the projections.

The actuator spring 6 may bear firstly against the sleeve 3, and secondly against the piston rod, e.g. against a fourth shoulder 58 that is axially offset from said third shoulder 53 towards the trailing portion 54. In the embodiment shown, the fourth shoulder 58 forms a base of the above-mentioned tubular portion.

The pivot members 7 are advantageously assembled in pivotable manner on the sleeve 3, and they are advantageously identical. Preferably, they are arranged on either side of the piston rod 5. They are not movable axially relative to said lower body 1, but only in pivoting about their pivot pins 79, which are parallel. In a variant, they could be assembled in some other way, in particular on the lower body 1 or on the upper body 2.

Each pivot member 7 may include a plurality of projections 71, 72, 73: a first projection 71 that is adapted to co-operate with the leading surface (in the axial travel direction of the piston rod during actuation) of the first radial projection 52 of the piston rod 5; a second projection 72 that is adapted to co-operate with the leading surface of the second radial projection 53; and a third projection 73 that is adapted to co-operate with the trailing surface of the second radial projection 53. Naturally, other embodiments can also be envisaged, e.g. with a different number of projections. Indentations could alternatively replace the projections.

The resilient elements 8 connect the two pivot members 7 together. The principle consists in combining two stationary pivot pins, in particular the pivot pins 79 of the two pivot members 7, with two movable pins, in particular the fastener points 78 of the pivot members 7 on which the resilient elements 8 are fastened.

Figure 4:
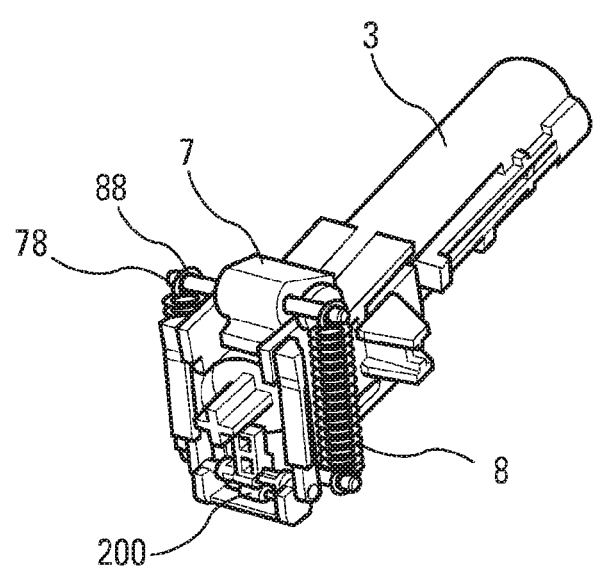
FIG. 4 is a view similar to the view in FIG. 3, as seen from below.

Thus, as can be seen in FIG. 4, the first resilient element 8 may be fastened firstly to a first fastener point of the first pivot member, and secondly to a first fastener point of the second pivot member, and the arrangement may be similar and symmetrical for the other resilient element. Preferably, each pivot member 7 includes a rod 78 having two projecting side edges. The first resilient element thus connects the first projecting edges together, and the second resilient element connects the second projecting edges together. Other variant embodiments are possible. Advantageously, when the resilient elements 8 are springs, they are identical and include eyelets 88 that are adapted to be fastened to said first and second projecting edges 78 of the pivot members 7. In a variant, the resilient elements could be different, e.g. in the form of O-rings or of other elements made of elastically-deformable material. The use of rings made of elastic material, such as O-rings, to replace the springs shown in the drawings make it possible, in particular, to reduce the amount of space the system occupies radially.

Thus, when the movable pins 78 are axially offset relative to the stationary pivot pins 79, they exert a force by means of the resilient elements 8.

When said movable pins 78 are arranged in front of said stationary pins 79 in the travel direction of the piston rod 5, the force opposes the pivoting imparted to said pivot members 7 by said piston rod 5. The pivoting of the pivot members 7 is thus braked by said resilient elements 8.

In contrast, when said movable pins 78 are arranged behind said stationary pins 79 in the travel direction of the piston rod 5, the force acts in the same direction as the pivoting imparted to said pivot members 7 by said piston rod 5. The pivoting of the pivot members 7 is thus amplified by said resilient elements 8.

When the stationary and movable pins 79, 78 are in alignment, there is a neutral point in which said resilient elements 8 do not influence the pivoting of the pivot members 7. It is in this position that the system toggles from a "braking" or "damping" state into an "amplification" state.

Such a force-adjustment system that is adapted to exert a force F1 and/or a force F2 on said piston rod 5. At the end of pricking the force F1 opposes the force exerted by the actuator spring 6 on the piston rod 5, so as to decrease the force exerted on said reservoir S by said piston rod 5 at the end of pricking. In contrast, at the beginning of injection, the force F2 is added to the force exerted by the actuator spring 6 on the piston rod 5, so as to amplify the force that is exerted on said piston P by said piston rod 5 at the beginning of injection. The force-adjustment system may exert only the force F1, only the force F2, or both of the forces F1 and F2.

FIGS. 5, 6, 7, 8, 9, 10, 11, 12, 13 and 14 show the actuation sequences of the FIG. 1 autoinjector.

Figures 5, 6, 7, 8, 9:
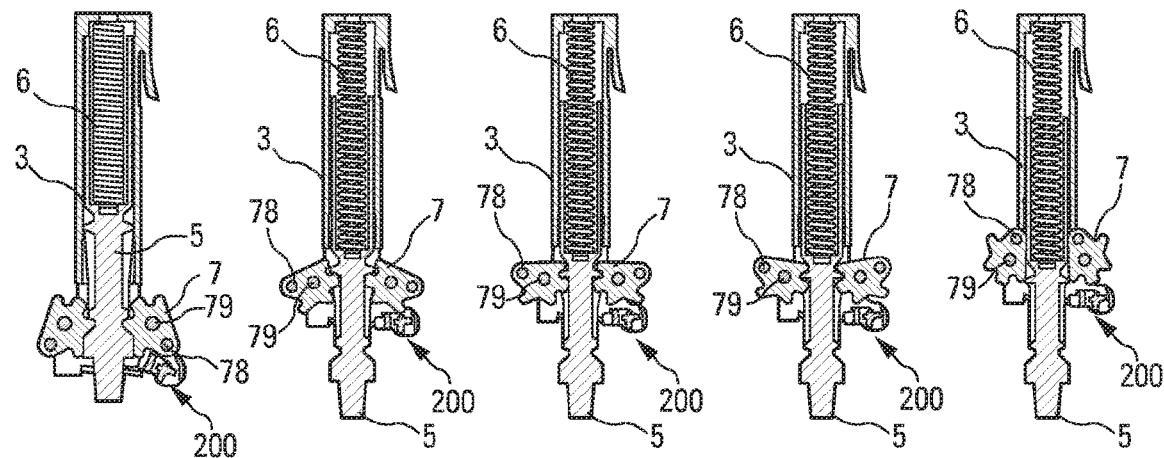
FIGS. 5, 6, 7, 8 and 9 are diagrammatic section views showing the successive sequences of the present invention, in the FIG. 1 embodiment.
Figures 10, 11, 12, 13, 14:
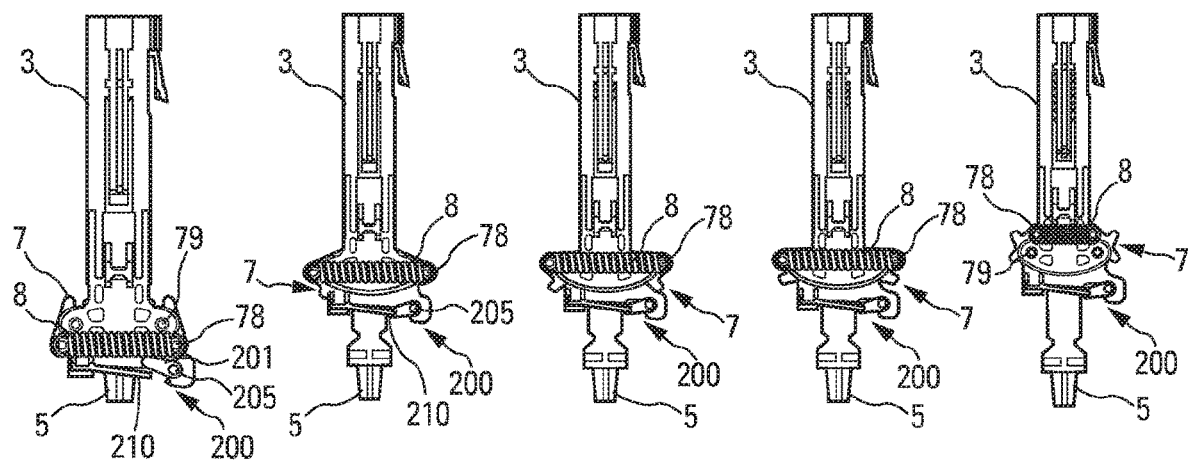
FIGS. 10, 11, 12, 13 and 14 are diagrammatic side views showing the successive sequences of FIGS. 5 to 9.

In FIGS. 5 and 10, the autoinjector is in the rest position prior to actuation. In this rest position, the needle of the syringe S is arranged inside the lower body 1. Said movable pins 78 are arranged in front of said stationary pins 79 in the travel direction of the piston rod 5. The actuator spring 6 urges the piston rod 5 towards the piston of the syringe S, but the piston rod 5 is held in the rest position by the first projection 71 of the pivot members 7 that co-operates with the first shoulder 51 of the piston rod 5. Under the pressure of the actuator spring 6, said first shoulder 51 of the piston rod 5 pushes the first projection 71 of the pivot members 7 in pivoting, but such pivoting is prevented by a locking system 200.

The locking system 200 may include at least one locking element that is movable and/or deformable between a locked position in which it prevents at least one pivot member 7 from pivoting, and an unlocked position in which said at least one pivot member 7 can pivot. Said locking element 201 is urged resiliently towards its locked position by a drive member 210, such as a resilient blade. Advantageously, said locking element 201 is mounted to pivot on said sleeve 3 of said body, about a pivot pin 205. In the embodiment shown, said locking element 201 comprises both a blocking portion 202 that co-operates directly with a pivot member 7, and also a control portion 203 that co-operates with an unlocking element 101 that is secured to the actuator sleeve 100. Preferably, said unlocking element 101 is formed by an axial projection of said actuator sleeve 100. The unlocking element could be made in some other way.

When the user wishes to use the autoinjector, the user takes hold of the device, e.g. at the upper body 2, and presses the actuator sleeve 100 against the part of the body where the injection is to be performed. The actuator sleeve 100 thus moves axially towards the inside of the lower body 1. When the stroke of said actuator sleeve 100 towards the inside of the lower body 1 is sufficient to enable co-operation between the locking element 201 and the unlocking element 101, the unlocking element 101 causes the locking element 201 of the locking system to pivot about its pin 205, which releases the pivot members 7. When the user relaxes the pressure on the actuator sleeve 100 without actuating the autoinjector via the actuator button 4, the resilient blade 210 returns the locking element 201 into its locked position. In particular, this enables the user to select the injection site by testing a plurality of locations without actuating the actuator button 4. When, after unlocking the pivot members 7 by pressing on the actuator sleeve 100, the user presses on the axial actuator button 4, thereby moving the piston rod 5 axially a little and causing the pivot members 7 to pivot and the autoinjector to be actuated.

Advantageously, said unlocking element 101 co-operates with said locking system 200 at the end of stroke of said actuator sleeve 100, between its initial rest position and its actuated position, in particular when said actuator sleeve 100 has performed at least 90% of said stroke. This makes it possible to stop actuating the autoinjector only when the user is certain that the fluid will be expelled at the desired injection depth, and thus avoids the risk of premature actuation at a depth that is too shallow.

The pivoting of the pivot members 7 generated by the actuation force causes the first projection 71 and the first shoulder 51 to disengage from each other. This thus releases the piston rod 5 that is then moved axially under the effect of the actuator spring 6. This causes the syringe S to move in the lower body 1 and thus causing pricking.

When the second projection 72 of the pivot members reaches the leading surface of the second radial projection 53 of the piston rod 5, the pricking stage is not completely terminated. This can be seen in FIGS. 6 and 11. At this moment, the leading surface of the second radial projection 53 causes the pivot members 7 to pivot still further by pushing on their second projections 72. This tensions or loads the resilient elements 8 still further, which elements thus oppose an increasing force against pivoting of the pivot members 7. This generates a "braking" or "damping" force. This generates damping at the end of pricking, by decreasing the force exerted by the piston rod 5 on the syringe S, thereby greatly improving the comfort of the user and avoiding damaging the collar of the syringe S. Naturally, the forces of the actuator spring 6 and of the resilient elements 8 are selected so that pricking is only damped without being stopped.

As the pivot members 7 pivot during the pricking stage, the resilient elements 8 become increasingly tensioned. Simultaneously, the movable pins 78 of the pivot members 7 move progressively towards the stationary pins 79. The device is advantageously adjusted so as to generate maximum torque at (or just prior to) the end of the pricking stage. The neutral point in which the movable and stationary pins are in alignment may thus be reached at (or just prior to) the end of the pricking stage.

When the pivot members 7 and the resilient elements 8 are in the neutral position, shown in FIGS. 7 and 12, the piston rod is still urged axially by the actuator spring 6. Thus, the neutral position is not stable, and the system toggles automatically from the state of braking pricking to the state of amplifying the beginning of injection. Optionally, the third projection 73 may be arranged relative to the second projection 72 so that, immediately after passing the neutral position, the pivot members 7 pivot a little under the effect of the tensioned resilient elements 8. This may enable an audible sound to be generated when said third projection 73 hits the second radial projection 53 of the piston rod, so as to inform the user of the beginning of the injection stage.

When the needle reaches its pricking position with the needle fully inserted, the injection stage is triggered, and this is shown in FIGS. 8 and 13. The leading end 55 of the piston rod then pushes on the piston under the effect of the force exerted by the actuator spring 6. During the entire injection stage, the piston rod 5 slides inside the syringe S, pushing the piston of said syringe under the effect of the spring 6. The fluid is thus dispensed through the needle.

At the beginning of the injection stage, the third projection 73 of each pivot member 7 thus comes into contact with the trailing surface of the second radial projection 53. As at the end of the pricking stage, the torque exerted by the system is at a maximum immediately after the neutral position, and the tensioned resilient elements 8 thus urge the pivot members 7 strongly in pivoting. This causes the force of the actuator spring 6 to be amplified at the beginning of the injection stage. This amplification increases the force exerted by the piston rod 5 on the piston, and thus makes it possible to guarantee that the piston starts to move from its rest position, without having to increase the force of the actuator spring 6. Specifically, the maximum resistance during the injection stage is created when starting movement of the piston. Once injection has begun, the friction of the piston in the syringe S, the viscosity of the fluid to be injected, and the resistance of the narrow passage of the needle are smaller and thus no longer require the same force from the actuator spring 6.

As can be seen in FIGS. 9 and 14, the pivot members 7 are disengaged from the piston rod after an injection stroke of the piston rod 5 that is relatively small, typically a few millimeters, e.g. about 4 millimeters (mm). From this disengagement, the system becomes inactive, and the injection of the fluid follows in the usual way. It may be envisaged to adapt the force-adjustment system so that it can amplify the force exerted on the piston for a greater fraction of the injection stroke, e.g. about 20 mm, or for the entire injection stroke, in particular with reservoirs having an axial dimension that is short.

FIGS. 29, 30, 31 and 32 show another advantageous embodiment of the autoinjector in which there is no automatic pricking, or auto-pricking. It should be observed that these figures are diagrammatic only and non-limiting of such an embodiment. In this embodiment, the actuator spring 6 performs injection only, by moving the piston rod 5, and thus the piston P, between the rest position and the injection position. In this embodiment, pricking is performed manually by means of the actuator sleeve 100. In this embodiment, the syringe S is thus stationary relative to the body of the autoinjector.

Figure 29:
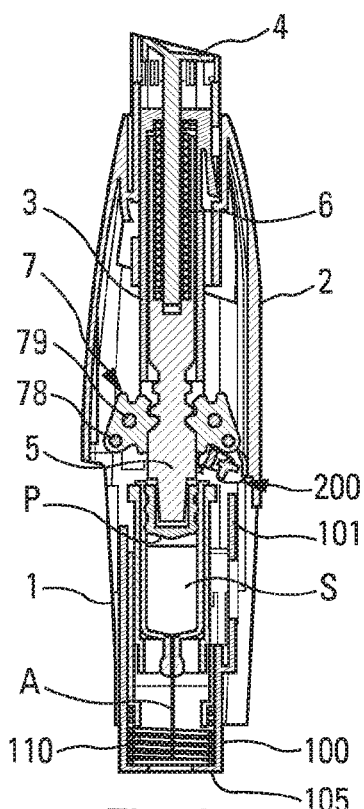
FIGS. 29, 30, 31 and 32 are section views showing still another embodiment of the invention.
Figure 30:
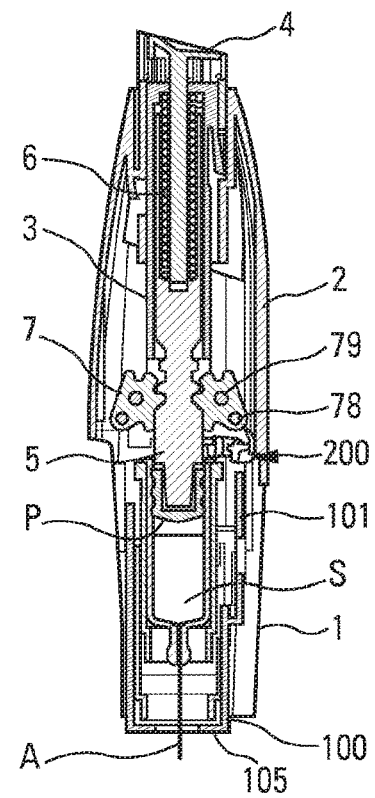
Figure 31:
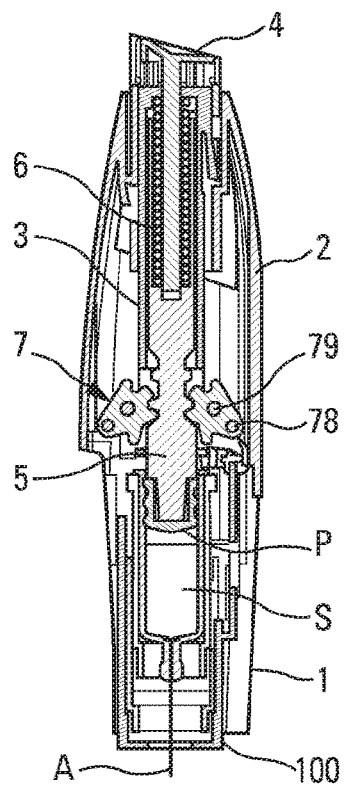
Figure 32:
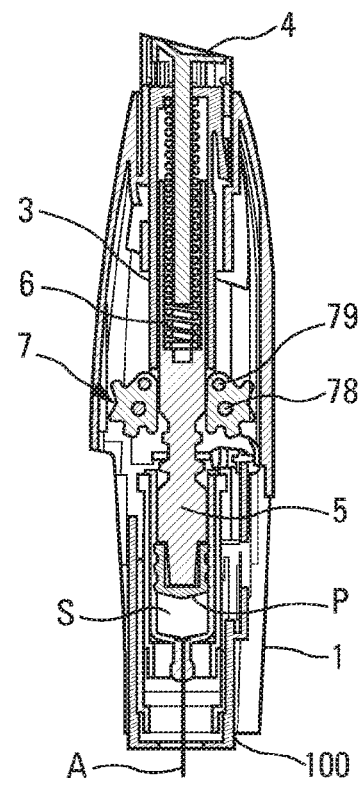

In the rest position shown in FIG. 29, the actuator sleeve 100, urged by its spring 110, surrounds the needle A of the syringe S. When the user wishes to actuate the autoinjector, the user places the axial end surface 105 of the actuator sleeve 100 against the injection site and presses on the autoinjector. The actuator sleeve 100 then slides axially towards the inside of the lower body 1, thus exposing the needle A of the syringe S that then penetrates into the body of the user, as can be seen in FIG. 20. The user may then actuate the axial button 4 so as to move the piston rod 5, and the force-adjustment system then becomes active as described above, acting via the pivot members 7 to exert an amplification force F2 on the piston rod 5 at the beginning of injection, as shown in FIG. 31. FIG. 32 shows the pivot members 7 disengaged from the piston rod 5, the end of injection thus continuing without any action from said pivot members. In a variant, it could be envisaged to cause the pivot members to act during the entire injection stage.

In this embodiment, the force-adjustment system thus exerts only the amplification force F2 at the beginning of injection, and does not intervene during pricking.

In the invention, the autoinjector includes a visual and/or audible indicator 300 for informing the user that injection has ended. The indicator includes an indication portion that comes to co-operate with at least one viewing window at the end of injection, so as to provide a visual indication. Advantageously, the indicator also provides an audible indication in addition to the above-mentioned visual indication. The invention that is described in greater detail below is equally applicable to the auto-pricking embodiment described with reference to FIGS. 1 to 14, and to the manual-pricking embodiment described with reference to FIGS. 29 to 32.

FIGS. 15, 16, 17, 18, 19, 20, 21 and 22 show a first embodiment of the invention, in which the indicator is formed by said sleeve 3.

Figure 21:
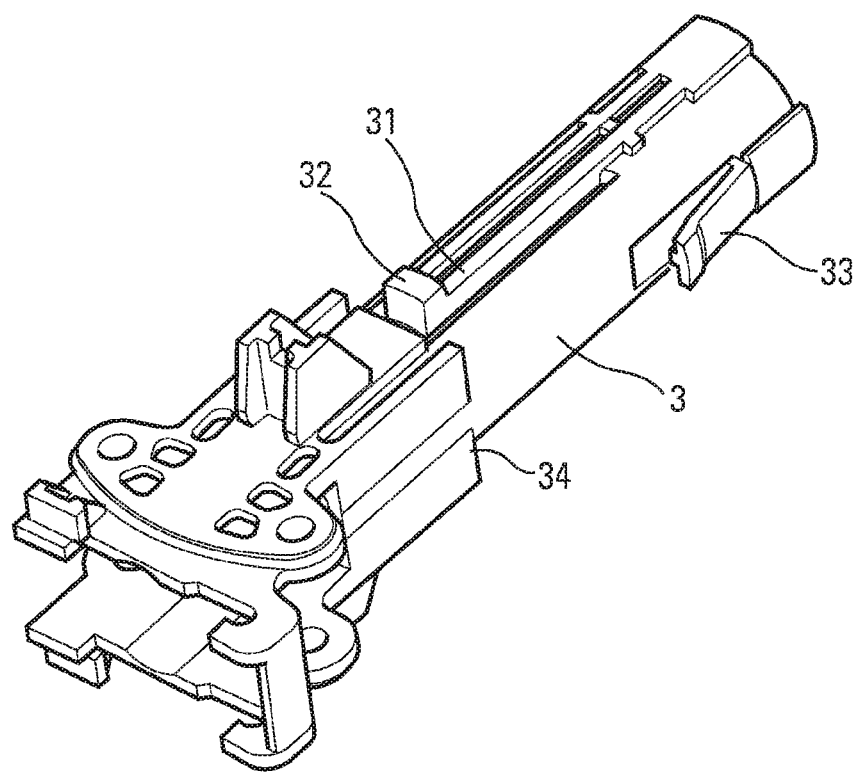
FIG. 21 is a perspective view of the sleeve in an advantageous embodiment of the present invention.
Figure 22:
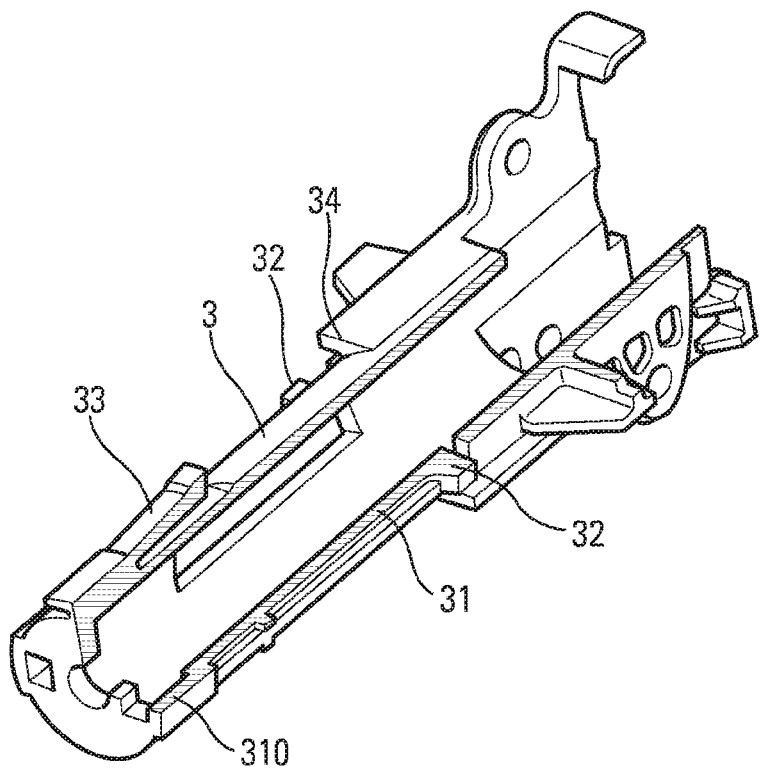
FIG. 22 is a cut-away perspective view of the FIG. 21 sleeve.

FIGS. 21 and 22 show the structure of said sleeve 3 in detail. In this embodiment, the indication portion is in formed by an axial end 310 of said sleeve 3, which axial end comes to co-operate at the end of injection with the viewing window(s) formed in the axial button 4, as can be seen in FIGS. 15 to 20. Advantageously, there are a plurality of viewing windows, e.g. two, three, or four, distributed around the axial peripheral edge of said axial button 4. The axial end 310 of the sleeve 3 thus forms an axial projection that is made integrally with the sleeve 3 and that comes to be positioned facing the viewing windows 400 at the end of injection.

The sleeve 3 includes at least one, and preferably two, axial tabs 31, each of which is radially deformable and provided with a head 32. The head 32 co-operates with a portion of the upper body 2, specifically an inner sleeve 25 of said upper body 2. Each axial tab 31 is deformable radially inwards, and prior to and during actuation is prevented from deforming by the piston rod 5, in particular a hollow sleeve 550 of said piston rod 5 that receives the actuator spring 6. During injection, the piston rod 5 moves axially relative to said sleeve 3, and, at the end of injection, the piston rod no longer blocks the axial tabs 31. The axial tabs may then deform radially inwards, as can be seen in FIG. 20. Thus, the head 32 is no longer held by the inner sleeve 25, and the sleeve 3 may then move axially relative to the upper body 2 under the effect of the spring 6, in the direction opposite to the direction of movement of the piston rod 5 during actuation. As a result, the axial end 310 comes to co-operate with the viewing windows 400 of the axial button 4.

During the axial movement of the sleeve 3 relative to the upper body 2, an audible indication is advantageously provided by a shoulder 34 that is formed on the sleeve 3, as can be seen in FIGS. 21 and 22, and that comes to strike a portion of the upper body 2, in particular said inner sleeve 25, thus generating a sound that is audible to the user.

Figure 23:
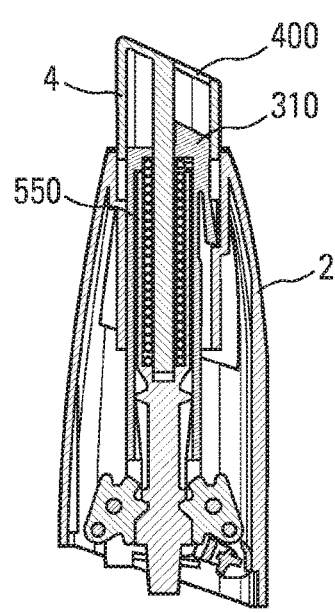
FIGS. 23, 24 and 25 show three other embodiments of a visual and/or audible indicator, in the rest position.
Figure 24:
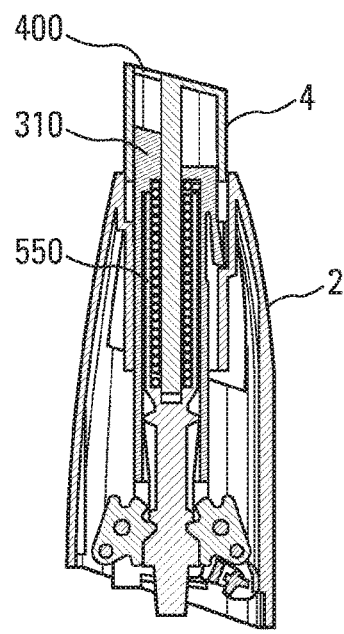
Figure 25:
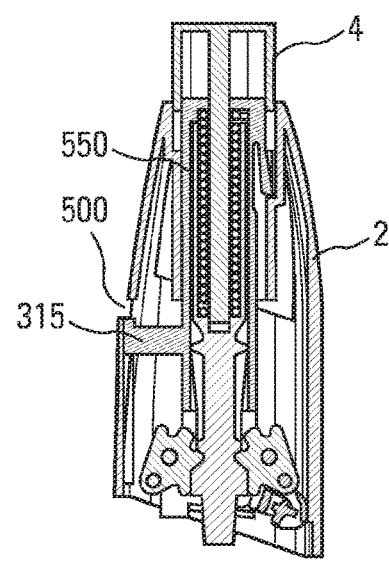

FIGS. 23, 24 and 25 show three variant embodiments.

In the embodiments in FIGS. 23 and 24, the axial end wall of the axial button 4 slopes, and the axial button 4 includes only a single viewing window 400. In the embodiment in FIG. 23, the viewing window is arranged in the lower portion of said sloping wall (in the position in FIG. 23), while in the embodiment in FIG. 24, it is arranged in the higher portion. Consequently, the axial end projection 310 of the sleeve 3 is adapted to have an appropriate shape for co-operating with said viewing window 400.

In the embodiment in FIG. 25, a viewing window 500 is not formed in the axial button 4, but in the body, specifically the upper body 2. In this configuration, the sleeve 3 includes an axial projection 315 that extends sideways relative to said sleeve, and that comes to co-operate with said window 500 at the end of injection.

Figure 26:
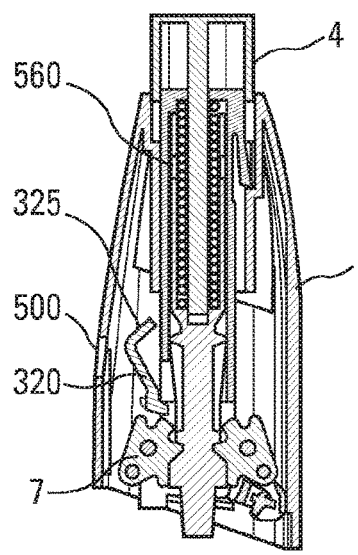
FIGS. 26, 27 and 28 are views similar to the views in FIGS. 15 to 17, showing still another embodiment of the present invention.
Figure 27:
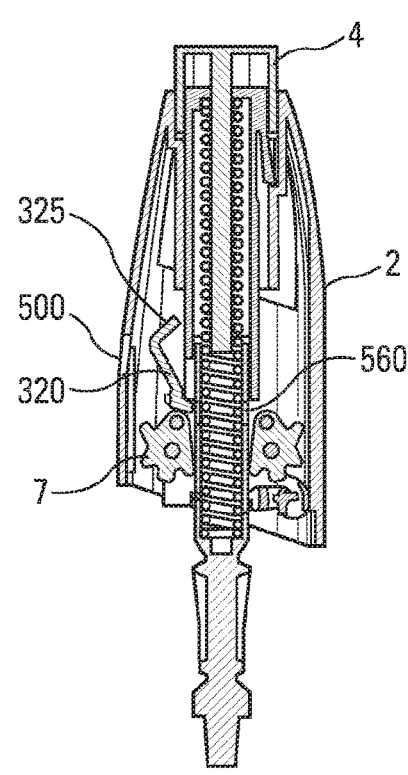
Figure 28:
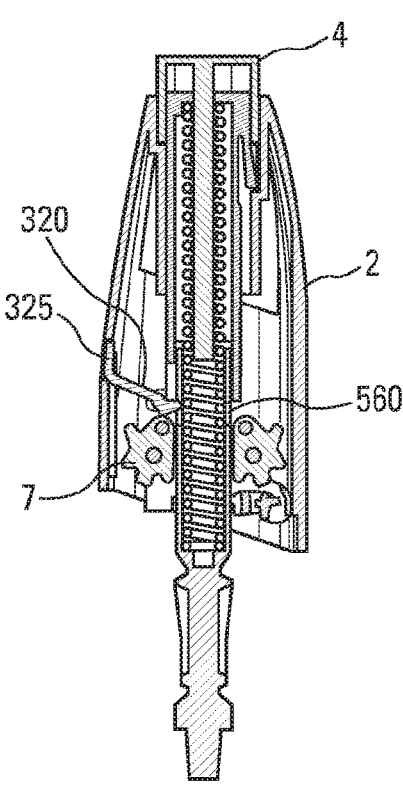

FIGS. 26 to 28 show another embodiment in which the indicator is not an integral part of the sleeve 3, but is pivotally mounted thereon. The viewing window 500 is formed in the upper body 2. A pivotable indicator element 320 is thus pivotally mounted on said sleeve 3, in the proximity of the pivot members 7. An end portion 325 of said pivotable indicator element 320 thus forms said indication portion of the indicator. Advantageously, said pivotable indicator element 320 is pivoted by said pivot members 7 at the end of injection. To do this, the piston rod 5 and in particular the hollow sleeve 550 may include an opening 560. During injection, the pivot members 7 cease meshing with the piston rod 5, but the springs 8 can maintain a certain amount of tension urging said pivot members to pivot. During the end of injection, the pivot members thus slide against the piston rod 5. When the opening 560 in the piston rod 5 comes level with said pivot members, as can be seen in FIG. 27, said pivot members pivot a little thereby causing the pivotable indicator element 320 to pivot, as shown in FIG. 28, so as to enable the indication portion 325 to co-operate with said window.

Naturally, other variant embodiments are also possible.

Typically, it is possible to obtain damping and/or amplification forces F1, F2 of about 30 newtons (N). Naturally, other damping and braking values could be obtained by selecting in appropriate manner the resilient elements 8, and by dimensioning in appropriate manner the pivot members 7.

The present invention applies to devices used in particular for treatment of auto-immune diseases, e.g. of the rheumatoid arthritis, multiple scleroses, Crohn's disease type, for treatment of cancer, for antiviral treatments, e.g. of the hepatitis type, for treatment of diabetes, for treatment of anemia, or for treatment of allergy attacks, e.g. in the event of anaphylactic shock.

Although the present invention is described above with reference to several advantageous embodiments, naturally various modifications are possible for the person skilled in the art, without going beyond the ambit of the present invention, as defined by the accompanying claims.

The invention claimed is:

1. An autoinjector comprising a body, and a reservoir containing fluid and including a piston and a needle said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force on said piston rod, said force adding to a force exerted by said actuator spring on said piston rod at the beginning of injection, so as to amplify a force exerted on said piston by said piston rod at the beginning of injection, said force-adjustment system comprising two pivot members that co-operate with said piston rod, said pivot members being connected together by two resilient elements, said body including a sleeve, said pivot members being pivotally mounted on said sleeve to pivot about stationary pins, said autoinjector comprising a visual and/or audible indicator that is adapted to inform a user that injection has ended, said indicator being formed by or fastened to said sleeve and including an indication portion that is movable and/or deformable relative to said body so as to co-operate with at least one viewing window of said autoinjector after the end of injection; and wherein each pivot member includes a plurality of projections that are adapted to co-operate with a plurality of radial projections of the piston rod.

2. An autoinjector according to claim 1, wherein said resilient elements are fastened to said pivot members via parallel movable pins that are formed on said pivot members.

3. The autoinjector according to claim 2, wherein the movable pins are rods having two side edges.

4. An autoinjector according to claim 2, wherein, when the piston rod moves towards its injection position, said movable pins are arranged behind said stationary pins in a travel direction of said piston rod, said resilient elements, at the beginning of travel of the piston rod towards its injection position, causing said pivot members to pivot in such a manner as to relax said resilient elements, thereby creating an amplification force at the beginning of injection.

5. An autoinjector according to claim 1, wherein during pricking, the piston rod co-operates with the piston of the reservoir so as to move said reservoir relative to the body.

6. An autoinjector according to claim 1, wherein, prior to injection, said piston rod is initially moved by said actuator spring between said rest position and a pricking position in which said piston rod has moved said reservoir relative to said body so as to perform pricking.

7. An autoinjector according to claim 6, wherein during pricking, the piston rod co-operates with the piston of the reservoir so as to move said reservoir relative to the body.

8. An autoinjector according to claim 1, wherein said at least one viewing window is formed in said body.

9. The autoinjector according to claim 1, wherein the reservoir containing fluid, piston and a needle form a pre-filled syringe.

10. The autoinjector according to claim 1, wherein, when the piston rod moves from its rest position towards a pricking position, said movable pins are arranged in front of said stationary pins in the travel direction of said piston rod, said piston rod, at the end of travel towards its pricking position, causing said pivot members to pivot so as to load said resilient elements, thereby creating a braking force at the end of pricking, said braking force being opposed, at the end of pricking, to the force exerted by said actuator spring on said piston rod, so as to decrease a net force exerted on said reservoir by said piston rod at the end of pricking.

11. An autoinjector comprising a body, and a reservoir containing fluid and including a piston and a needle, said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force on said piston rod, said force adding to a force exerted by said actuator spring on said piston rod at the beginning of injection, so as to amplify a force exerted on said piston by said piston rod at the beginning of injection, said force-adjustment system comprising two pivot members that co-operate with said piston rod, said pivot members being connected together by two resilient elements, said body including a sleeve, said pivot members being pivotally mounted on said sleeve to pivot about stationary pins, said autoinjector comprising a visual and/or audible indicator that is adapted to inform a user that injection has ended, said indicator being formed by or fastened to said sleeve and including an indication portion that is movable and/or deformable relative to said body so as to co-operate with at least one viewing window of said autoinjector after the end of injection;

wherein said resilient elements are fastened to said pivot members via parallel movable pins that are formed on said pivot members;

wherein, prior to injection, said piston rod is initially moved by said actuator spring between said rest position and a pricking position in which said piston rod has moved said reservoir relative to said body so as to perform pricking; and wherein, when the piston rod moves from its rest position towards its pricking position, said movable pins are arranged in front of said stationary pins in the travel direction of said piston rod, said piston rod, at the end of travel towards its pricking position, causing said pivot members to pivot so as to load said resilient elements, thereby creating a braking force at the end of pricking, said braking force being opposed, at the end of pricking, to the force exerted by said actuator spring on said piston rod, so as to decrease a net force exerted on said reservoir by said piston rod at the end of pricking.

12. An autoinjector comprising a body, and a reservoir containing fluid and including a piston and a needle, said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force on said piston rod, said force adding to a force exerted by said actuator spring on said piston rod at the beginning of injection, so as to amplify a force exerted on said piston by said piston rod at the beginning of injection, said force-adjustment system comprising two pivot members that co-operate with said piston rod, said pivot members being connected together by two resilient elements, said body including a sleeve, said pivot members being pivotally mounted on said sleeve to pivot about stationary pins, said autoinjector comprising a visual and/or audible indicator that is adapted to inform a user that injection has ended, said indicator being formed by or fastened to said sleeve and including an indication portion that is movable and/or deformable relative to said body so as to co-operate with at least one viewing window of said autoinjector after the end of injection; and wherein said autoinjector is actuated by an axial button.

13. An autoinjector according to claim 12, wherein said at least one viewing window is formed in said axial button.

14. An autoinjector according to claim 13, wherein said at least one viewing window is arranged in a sloping axial end wall of said axial button.

15. An autoinjector according to claim 13, wherein said at least one viewing window comprises a plurality of viewing windows, distributed around an outer axial end edge of said axial button.

16. An autoinjector comprising a body, and a reservoir containing fluid and including a piston and a needle, said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force on said piston rod, said force adding to a force exerted by said actuator spring on said piston rod at the beginning of injection, so as to amplify a force exerted on said piston by said piston rod at the beginning of injection, said force-adjustment system comprising two pivot members that co-operate with said piston rod, said pivot members being connected together by two resilient elements, said body including a sleeve, said pivot members being pivotally mounted on said sleeve to pivot about stationary pins, said autoinjector comprising a visual and/or audible indicator that is adapted to inform a user that injection has ended, said indicator being formed by or fastened to said sleeve and including an indication portion that is movable and/or deformable relative to said body so as to co-operate with at least one viewing window of said autoinjector after the end of injection; and wherein said indicator is formed by said sleeve, including a single-piece axial projection that forms said indication portion of the indicator.

17. An autoinjector comprising a body, and a reservoir containing fluid and including a piston and a needle, said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force on said piston rod, said force adding to a force exerted by said actuator spring on said piston rod at the beginning of injection, so as to amplify a force exerted on said piston by said piston rod at the beginning of injection, said force-adjustment system comprising two pivot members that co-operate with said piston rod, said pivot members being connected together by two resilient elements, said body including a sleeve, said pivot members being pivotally mounted on said sleeve to pivot about stationary pins, said autoinjector comprising a visual and/or audible indicator that is adapted to inform a user that injection has ended, said indicator being formed by or fastened to said sleeve and including an indication portion that is movable and/or deformable relative to said body so as to co-operate with at least one viewing window of said autoinjector after the end of injection; and wherein said indicator is formed by a pivotable indicator element that is pivotally mounted on said sleeve, an end portion of said pivotable indicator element forming said indication portion of the indicator.

18. An autoinjector according to claim 17, wherein said pivotable indicator element is pivoted by said pivot members at the end of injection.

19. An autoinjector comprising a body, and a reservoir containing fluid and including a piston and a needle, said autoinjector further comprising a piston rod that is adapted to co-operate with the piston of said reservoir, said piston rod being movable between a rest position and an injection position in which said piston rod has moved the piston of the reservoir so as to inject the fluid through the needle, an actuator spring being provided so as to urge said piston rod towards its injection position, the autoinjector further comprising a force-adjustment system that is adapted to exert at least one force on said piston rod, said force adding to a force exerted by said actuator spring on said piston rod at the beginning of injection, so as to amplify a force exerted on said piston by said piston rod at the beginning of injection, said force-adjustment system comprising two pivot members that co-operate with said piston rod, said pivot members being connected together by two resilient elements, said body including a sleeve, said pivot members being pivotally mounted on said sleeve to pivot about stationary pins, said autoinjector comprising a visual and/or audible indicator that is adapted to inform a user that injection has ended, said indicator being formed by or fastened to said sleeve and including an indication portion that is movable and/or deformable relative to said body so as to co-operate with at least one viewing window of said autoinjector after the end of injection; and wherein said sleeve includes at least one axial tab that is radially deformable and that co-operates with said body, said axial tab being prevented from deforming by said piston rod prior to and during movement of said piston rod, thus blocking any axial movement of said sleeve relative to said body, said piston rod releasing said blocking at the end of injection, such that said axial tab deforms radially inwards, enabling said sleeve to move axially relative to said body so as to provide a visual and/or audible indication.

* * * * *